US009931076B2

United States Patent
Gu

(10) Patent No.: US 9,931,076 B2
(45) Date of Patent: Apr. 3, 2018

(54) METHOD AND DEVICE FOR TONOMETRIC BLOOD PRESSURE MEASUREMENT

(71) Applicant: Hong Kong Applied Science and Technology Research Institute Company Limited, Hong Kong (HK)

(72) Inventor: Wenbo Gu, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 960 days.

(21) Appl. No.: 14/307,503

(22) Filed: Jun. 18, 2014

(65) Prior Publication Data

US 2015/0366464 A1    Dec. 24, 2015

(51) Int. Cl.
*A61B 5/021*    (2006.01)
*A61B 5/00*    (2006.01)

(52) U.S. Cl.
CPC ............ *A61B 5/489* (2013.01); *A61B 5/0022* (2013.01); *A61B 5/0064* (2013.01); *A61B 5/02116* (2013.01)

(58) Field of Classification Search
CPC ..... A61B 5/489; A61B 5/0022; A61B 5/0064; A61B 5/02116
USPC .......................... 600/481, 483, 485, 490–499
See application file for complete search history.

(56) References Cited

U.S. PATENT DOCUMENTS

| 6,662,130 B1* | 12/2003 | Peel, III | A61B 5/021 600/485 |
| 6,730,038 B2* | 5/2004 | Gallant | A61B 5/021 600/485 |
| 6,974,419 B1* | 12/2005 | Voss | A61B 5/022 600/485 |

(Continued)

FOREIGN PATENT DOCUMENTS

CN    102613966 A    8/2012

OTHER PUBLICATIONS

First Office Action with Search Report of CN201410273599.6 issued by the State Intellectual Property Office of China dated Jul. 7, 2015.

(Continued)

*Primary Examiner* — Navin Natnithithadha
(74) *Attorney, Agent, or Firm* — Spruson & Ferguson (Hong Kong) Limited

(57) ABSTRACT

A method for determining an artery location on a living subject's skin and positioning a tonometry pressure sensor on the artery location for tonometric blood pressure measurement is provided. The method comprises a non-contact optical search followed by a contact pressure search. In the non-contact optical search, an optical-sensing unit is used to scan the skin along a scan path while maintaining a predetermined distance between the unit and the scan path. A search region within the scan path and a height profile characterizing the scan path's curvature are determined. The search region is determined such that an artery is predicted to lie thereunder. The artery location is then searched within (Continued)

the search region by the contact pressure search, in which the pressure sensor sweeps along the search region and the sweeping is guided by curvature information provided by the height profile. A device using the method is also provided.

20 Claims, 8 Drawing Sheets

(56) References Cited

U.S. PATENT DOCUMENTS

| | | | |
|---|---|---|---|
| 7,048,691 B2 * | 5/2006 | Miele | A61B 5/02028 600/465 |
| 7,291,112 B2 * | 11/2007 | Martin | A61B 5/022 600/485 |
| 7,503,896 B2 * | 3/2009 | Miele | A61B 5/02028 600/301 |
| 7,771,361 B2 | 8/2010 | Bae et al. | |
| 7,867,170 B2 * | 1/2011 | Gallant | A61B 5/021 600/485 |
| 7,946,994 B2 * | 5/2011 | Finburgh | A61B 5/022 600/485 |
| 7,955,267 B2 * | 6/2011 | Voss | A61B 5/022 600/485 |
| 7,976,471 B2 * | 7/2011 | Martin | A61B 5/0048 600/485 |
| 8,328,727 B2 * | 12/2012 | Miele | A61B 5/02028 600/437 |
| 8,597,195 B2 | 12/2013 | Gallant et al. | |
| 8,945,016 B2 * | 2/2015 | Voss | A61B 5/022 600/481 |
| 8,961,426 B2 * | 2/2015 | Martin | A61B 5/0048 600/500 |
| 2002/0055680 A1 * | 5/2002 | Miele | A61B 5/02028 600/450 |
| 2002/0062086 A1 * | 5/2002 | Miele | A61B 5/02028 600/483 |
| 2004/0059234 A1 * | 3/2004 | Martin | A61B 5/022 600/500 |
| 2005/0038346 A1 * | 2/2005 | Miele | A61B 5/02028 600/485 |
| 2006/0094965 A1 * | 5/2006 | Voss | A61B 5/022 600/485 |
| 2007/0197887 A1 * | 8/2007 | Lunak | A61B 5/02055 600/323 |
| 2008/0021334 A1 * | 1/2008 | Finburgh | A61B 5/02028 600/490 |
| 2008/0064968 A1 * | 3/2008 | Martin | A61B 5/0048 600/493 |
| 2009/0069698 A1 | 3/2009 | Bae et al. | |
| 2009/0131806 A1 * | 5/2009 | Finburgh | A61B 5/022 600/485 |
| 2010/0286538 A1 | 11/2010 | Kim et al. | |
| 2011/0166458 A1 * | 7/2011 | Gallant | A61B 5/021 600/485 |
| 2011/0237961 A1 * | 9/2011 | Voss | A61B 5/022 600/485 |

OTHER PUBLICATIONS

International Search Report and Written Opinion of PCT/CN2015/078549 issued by the State Intellectual Property Office of China dated Jul. 28, 2015.

* cited by examiner

Note. HD pressure = Hold-down pressure

METHOD AND DEVICE FOR TONOMETRIC BLOOD PRESSURE MEASUREMENT

FIELD OF THE INVENTION

The present invention generally relates to tonometric blood pressure measurement. Particularly, this invention relates to a method for rapidly identifying an artery location and positioning a pressure sensor thereon for making such measurement, and a device using this method.

BACKGROUND

Tonometric blood pressure measurement is a non-invasive means for continuously monitoring blood pressure (BP) and obtaining additional cardiovascular parameters such as arterial stiffness, cardiac output and stroke volume. Before making such measurement, an accurate position of an artery location is required to be identified over a person's skin.

It is possible to use a single pressure sensor to search for the artery location when the sensor presses on the skin, as in U.S. Pat. No. 8,597,195. During the search, a constant hold-down pressure exerted by the sensor on the skin is required to be maintained. Due to the curvature of a body part under measurement, such as a wrist of a person, the sensor is required to finely and dynamically adjust its position to keep a constant hold-down pressure during the search. A long search time is usually resulted. U.S. Pat. No. 7,771,361 and US20100286538 suggest using an array of optical and pressure sensors to press on the skin to thereby identify the artery location. Although the search time is shorter, accuracy of the artery location is limited by the sensor dimension. High accuracy is achievable only with a small sensor size, the implementation of which is costly.

There is a need in the art for rapid and accurate identification of the artery location without a need to reduce the sensor dimension.

SUMMARY OF THE INVENTION

An aspect of the present invention is a method for determining an artery location on a living subject's skin and positioning a tonometry pressure sensor on the artery location. In the method, a non-contact optical search and a contact pressure search are performed. An optical-sensing unit having a light source and an optical detector is employed in a non-contact process to scan the skin along a scan path thereon in order to determine a search region within the scan path. The search region is determined such that an artery is predicted to lie thereunder. The artery location is then searched within the search region by a contact-based process of sweeping the pressure sensor along the search region.

The non-contact process further determines a height profile characterizing the scan path's curvature. The sweeping of the pressure sensor is guided by curvature information provided by the height profile.

In the non-contact process, the optical-sensing unit progressively scans the skin along the scan path with a light beam generated by the light source and configured for blood sensing while the optical detector measures an instantaneous power level of the light beam reflected from the skin and a body section thereunder so that a time sequence of the measured power levels is obtained after the scanning is done. The search region is searched and identified within the scan path according to the time sequence of the measured power levels. During the scanning, the optical-sensing unit's position is controlled to maintain a pre-determined distance between the unit and the scan path for eliminating a nuisance factor in obtaining the time sequence of the measured power levels. After the scanning is done, a time history of the unit's coordinates is obtained and the height profile is derived therefrom.

During the scanning of the skin, preferably an instantaneous distance of the light source from the scan path is estimated by one or more selected instantaneous power levels that have been measured so as to feedback-control the unit's position to maintain the pre-determined distance between the unit and the scan path.

In the contact-based process, the pressure sensor is positioned onto the search region with a hold-down pressure to be within a pre-determined pressure range. A first initial coordinate of the search region for the pressure sensor to directly move to is determined according to the height profile, thereby allowing the hold-down pressure to be attained by fine-positioning the pressure sensor around the first initial coordinate. The pressure sensor then progressively sweeps along the search region to measure a pressure pulse amplitude generated by the artery so that a sequence of measured amplitudes is obtained after the sweeping is done. During the sweeping, plural second initial coordinates of the search region for the pressure sensor to move to are determined according to the height profile. Within the search region, the artery location is determined from the obtained sequence of measured amplitudes to thereby allow the pressure sensor to be positioned on the artery location for blood pressure measurement.

A tonometric BP monitoring device is realizable by including a pressure sensor, a light source and an optical detector, and by configuring the device to determine an artery location and position the pressure sensor thereon according to the method disclosed herein.

Other aspects of the present invention are disclosed as illustrated by the embodiments hereinafter.

DETAILED DESCRIPTION

As used herein in the specification and appended claims, "a DC component" of a plurality of data is an average value of the data. It is also used herein that "an AC component" of a sequence of original data is a sequence of computed data each of which is an original data minus the DC component of the sequence of original data.

If a single pressure sensor is used in searching for an artery location over a person's skin, a pre-determined hold-down pressure exerted by the sensor on the skin is required to be maintained by fine-adjusting the sensor's position. The non-flat curvature of the skin necessitates the pressure sensor to test a lot of fine positions in verifying if the desired hold-down pressure is exerted, thereby significantly increasing the search time. The present invention achieves a reduced search time by decomposing the search into a first stage of determining a search region by a non-contact optical search for coarsely identifying an artery location, and a second stage of contact pressure search for finely identifying the artery location within the search region. Testing whether a desired hold-down pressure is exerted is required only in the second stage. To further reduce the search time, the first stage maps the curvature of the skin, and the resultant map is used in the second stage to enable a pressure sensor to quickly land on the skin and to follow the skin's curvature during scanning the search region so that the number of times in fine-positioning the pressure sensor for hold-down pressure verification is minimized.

An aspect of the present invention is to provide a method for determining an artery location on a living subject's skin and positioning a tonometry pressure sensor on the artery location for measuring BP of the living subject. The living subject can be a person and, as in many instances of medical examination, the artery location to be searched may be confined to an area of the skin on a hand or a wrist of the person. However, the present invention is not limited only to a human wrist in locating an artery. The present invention is applicable for other parts of a human body such as a neck. The living subject may also be an animal such as a horse.

Figure 1:
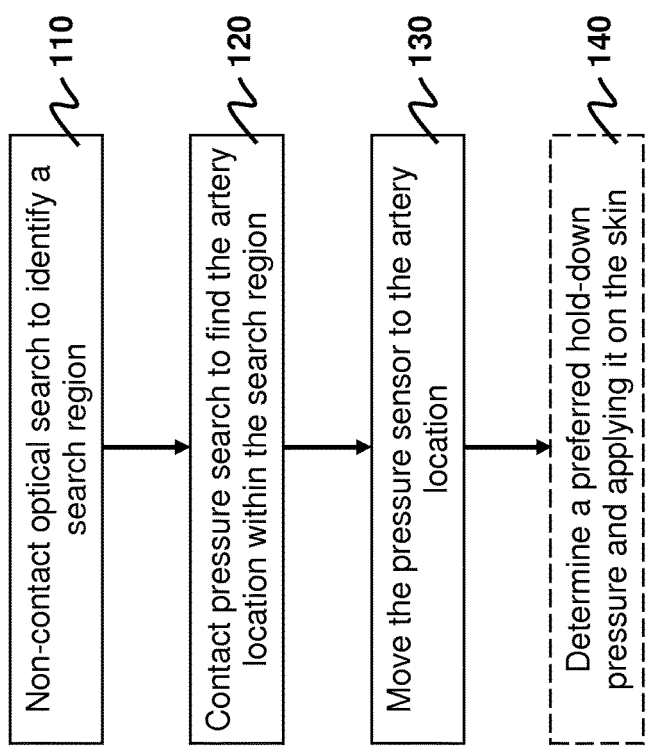
FIG. 1 depicts the steps in an exemplary method of the present invention.
Figure 3:
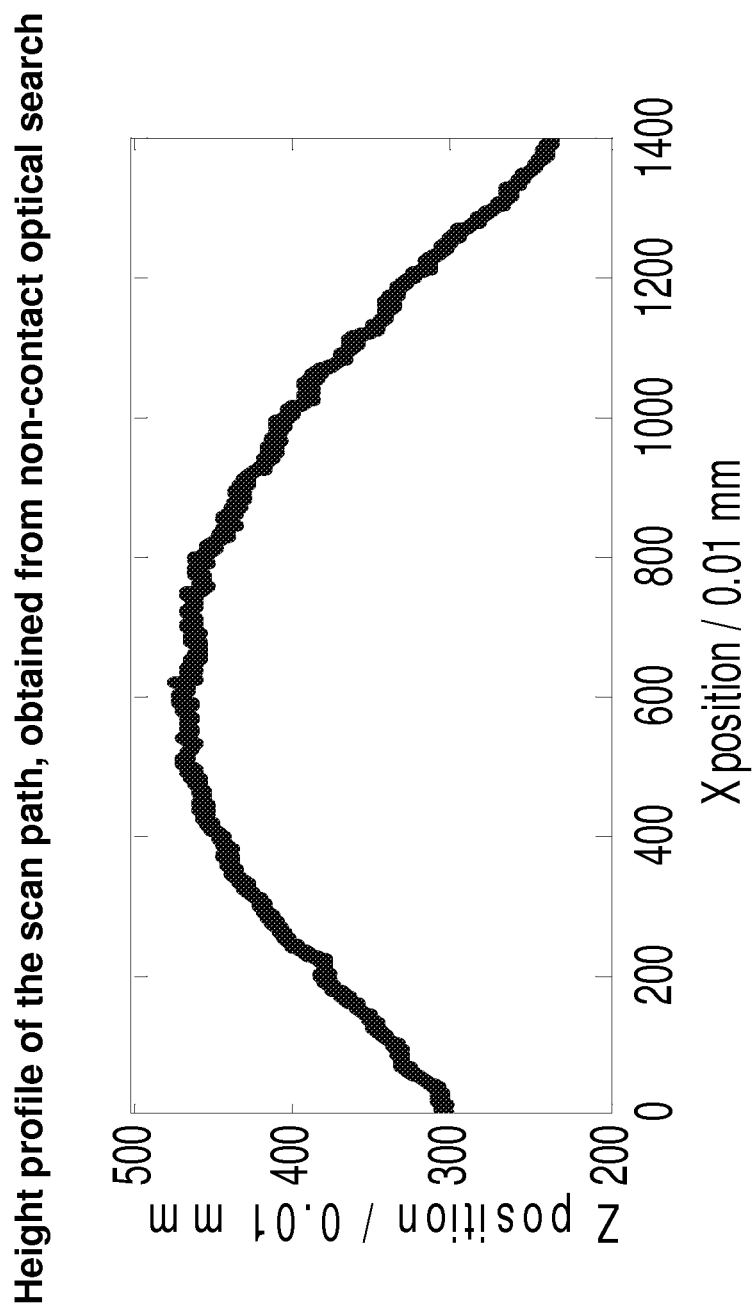
FIG. 3 is an example of a height profile obtained from the non-contact optical search.

Exemplarily, the method is illustrated with the steps thereof depicted in FIG. 1. The method employs an optical-sensing unit having a light source and an optical detector. The method comprises a non-contact optical search followed by a contact pressure search. A non-contact process 110 of using the optical-sensing unit to scan the skin along a scan path on the skin is first performed in order to determine a search region within the scan path. The search region is determined such that an artery is predicted to lie thereunder. The non-contact process 110 further determines a height profile of the scan path. The height profile is a map obtained in mapping the scan path's curvature, and characterizes a distance-height relationship along the scan path. In one form, the height profile is represented as a set of coordinates describing the skin's two-dimensional geometric positions along the scan path. An example of such height profile is shown in FIG. 3. After the non-contact process 110 is done, the artery location is searched within the search region by a contact-based process 120 of sweeping the pressure sensor along the search region. The sweeping is guided by curvature information provided by the height profile. That is, the height profile provides a next location's coordinate for the pressure sensor to move to during the sweeping such that the pressure sensor closely follows the skin's curvature in the sweeping. Note that the non-contact process 110 and the contact-based process 120 are for the non-contact optical search and the contact pressure search, respectively, mentioned above. Afterwards, the pressure sensor is moved to and positioned on the artery location, as in a step 130, for doing BP measurement, which may be preceded by a step 140 of determining a preferred hold-down pressure and applying it to the skin.

Figure 2:
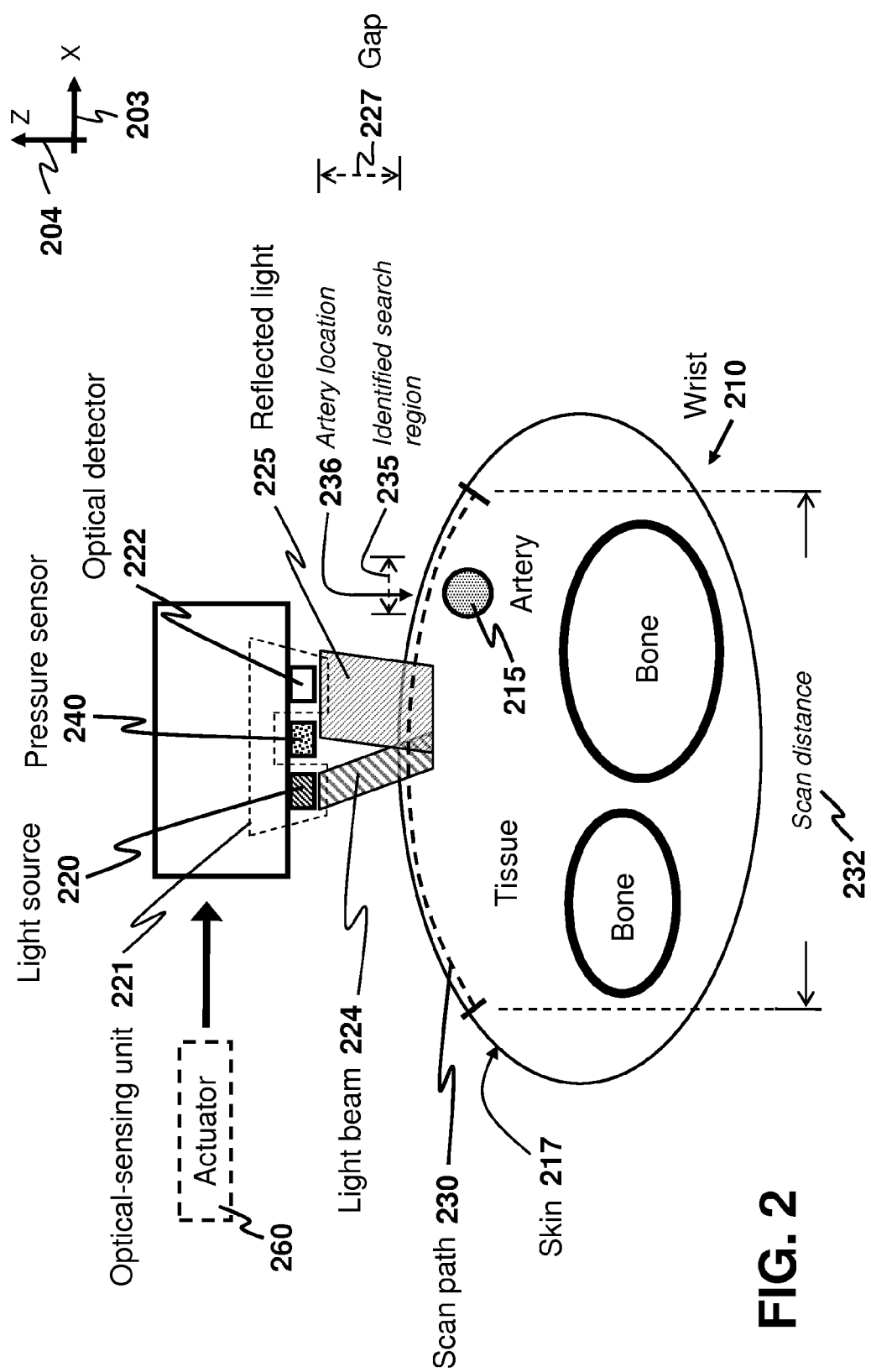
FIG. 2 depicts an arrangement of identifying an artery location according to the exemplary method of the present invention.

The two processes 110, 120 are exemplarily illustrated with an aid of FIG. 2, which shows an arrangement for identifying an artery location 236. For illustration purpose, a wrist 210 is considered in searching for an artery 215 therein; the present invention is not limited to identifying an artery location on a human wrist only.

In the non-contact process 110, an optical-sensing unit 221 comprising a light source 220 and an optical detector 222 progressively scans a living subject's skin 217 along a scan path 230 thereon with a light beam 224 generated by the light source 220 and configured for blood sensing while the optical detector 222 measures an instantaneous power level of reflected light 225, which is a part of the light beam 224 reflected from the skin 217 and a body section thereunder. Preferably the light beam 224 comprises an infrared light component responsive to the presence of blood by optical absorption. After the scanning is done, a time sequence of measured power levels is obtained, from which a search region 235 within the scan path 230 is identified.

In practical implementation, the scanning is usually done along an X-direction 203, i.e. a reference horizontal direction. For the human wrist 210, a straight-line scan distance 232 between 15 mm to 20 mm measured in the X-direction 203 is usually sufficient for the scanning of the scan path 230 in order to search for the artery 215, which generally has a diameter of 2 mm to 3 mm. Despite this size of the artery 215, an effective measurement range is only around 0.5 mm.

As is mentioned above, the accuracy of identifying the artery location 236 by an optical sensor is determined by its size. To avoid a need for an ultra-small optical sensor, practically the search region 235 may be set with a length of 3 mm to 4 mm. Preferably the light beam 224 is a collimated one with a beam size not greater than 2 mm if a search length of 3 mm to 4 mm is selected.

Due to non-contact scanning, there is a gap 227 between the optical-sensing unit 221 and the skin 217. Note that the instantaneous power level measured at the optical detector 222 is affected by the length of the gap 227. If such length varies during the scanning, this fluctuation causes a nuisance factor in obtaining the measured power levels, making analysis of the resultant time sequence difficult. Hence, during the scanning, it is required to control the position of the optical-sensing unit 221 to maintain a pre-determined distance, measured in a Z-direction 204, i.e. in a reference vertical direction, between the unit 221 and the scan path 230 for eliminating the nuisance factor. In one embodiment, the pre-determined distance is selected between 1 mm to 2 mm. An additional advantage of maintaining this distance is that after the scanning is done, a time history of coordinates traveled by the unit 221 is obtained and a height profile of the scan path 230 can be derived therefrom.

The optical-sensing unit 221 can be controlled to maintain the pre-determined distance from the skin 217 by, for example, first using a laser-based technique to measure the length of the gap 227. Despite this, an implement cost is reducible by using the optical-sensing unit 221 to measure the length of the gap 227 in addition to identifying the search region 235. It is first noticed that body materials that absorb the light beam 224 include blood, tissue and bone, and that pulses of blood travel through the artery 215 at different time instants. It is also noted that motion of the blood pulses causes a time-varying component, i.e. an AC component, in the time sequence of measured power levels. Removing this AC component from the time sequence gives a DC component, which is determined by tissue, bone, and non-pulsing blood flowing in veins, as well as by the length of the gap 227. As the skin reflection dominates the DC component and it attenuates quickly with the increase of gap length, the length of the gap 227 can be estimated by the DC component.

It follows that maintaining the pre-determined distance between the optical-sensing unit 221 and the scan path 230 is achievable by, during the scanning of the skin 217, estimating an instantaneous distance of the light source 220 from the scan path 230 by one or more selected instantaneous power levels that have been measured and then using the estimated instantaneous distance in a feedback control loop to adjust the unit 221's position. Preferably, the instantaneous distance is estimated according to a DC component computed from the one or more selected instantaneous power levels.

In maintaining the pre-determined distance for the gap 127 by the feedback control loop, the time history of coordinates traveled by the unit 221 is recorded. FIG. 3 shows an example of the height profile computed from this time history, which is in turn obtained according to the instantaneous distances computed from the aforementioned DC components.

Figure 4:
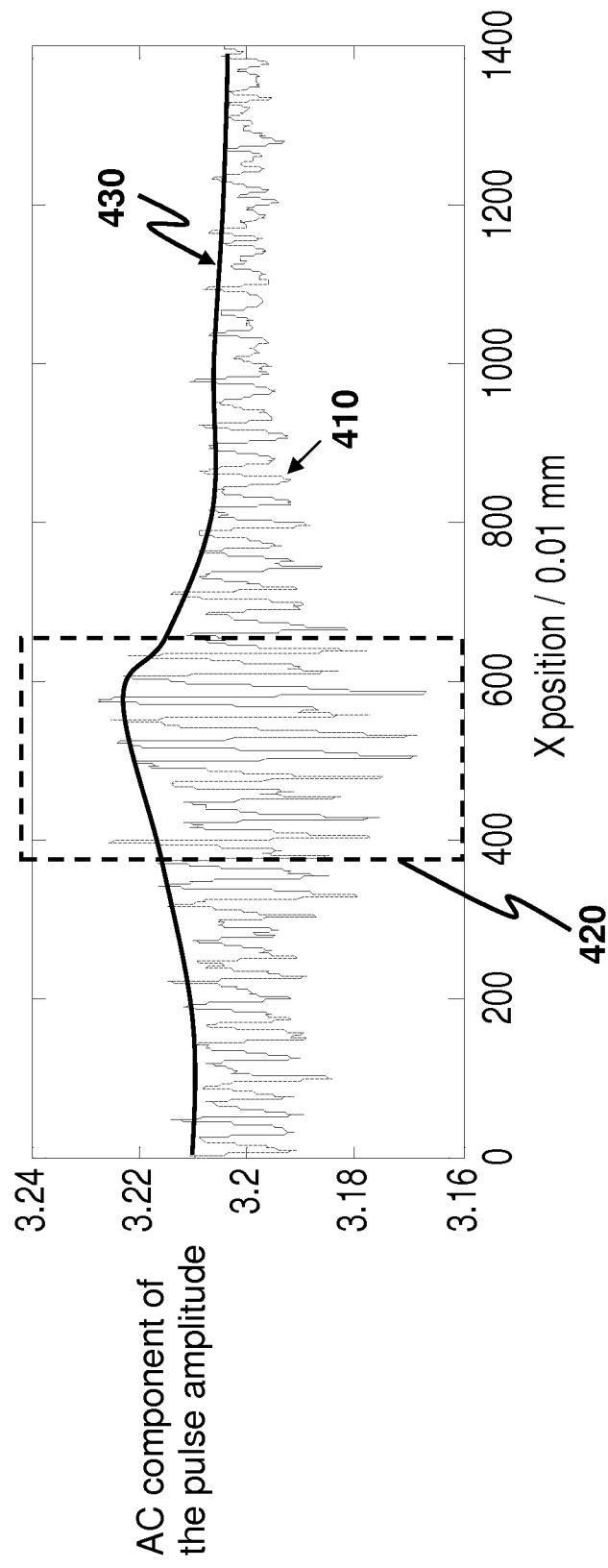
FIG. 4 is an example showing an AC component of pulse amplitude detected by an optical detector, indicating how the artery location is identifiable from the AC component.

FIG. 4 shows an example of identifying a search region 420 through computing AC components of a sequence 410 of measured power levels. The fluctuation in the AC components over positions along the X-direction 203 is due to pulsing of blood through the artery 215. An envelope 430 is computable from the sequence 410. The search region 420 is selected to be a window of ~3 mm enclosing the greatest amplitude in the envelope 430.

In the contact-based process 120, a pressure sensor 240 is moved in the Z-direction 204 and is positioned onto the search region 235 with a hold-down pressure set within a pre-determined pressure range. This pressure range may be set as a small range around a nominal value. The nominal value is a desired value of the hold-down pressure. This desired value may be a value selected from 30 mmHg to 100 mmHg in general. For example, the desired value may be set at 50 mmHg. The small range around the nominal value is a tolerance level within which a small variation of the hold-down pressure exerted by the pressure sensor 240 is permissible. An XZ coordinate that the pressure sensor 240 lands on or directly moves to the search region 235 is termed a first initial coordinate and is determined by the height profile. Then the hold-down pressure can be attained by fine-positioning the pressure sensor 240 along the Z-direction 204 around this initial coordinate. Afterwards, the pressure sensor 240 is driven to progressively sweep along the search region 235 to measure a pressure pulse amplitude generated by the artery 215. A sequence of measured amplitudes is obtained after the sweeping is done. During the sweeping along the search region 235, plural XZ coordinates for the pressure sensor 240 to move to are determined according to the height profile, these XZ coordinates being termed second initial coordinates. Within the search region 235, the artery location 236 is determined from the obtained sequence of measured amplitudes.

Figure 5:
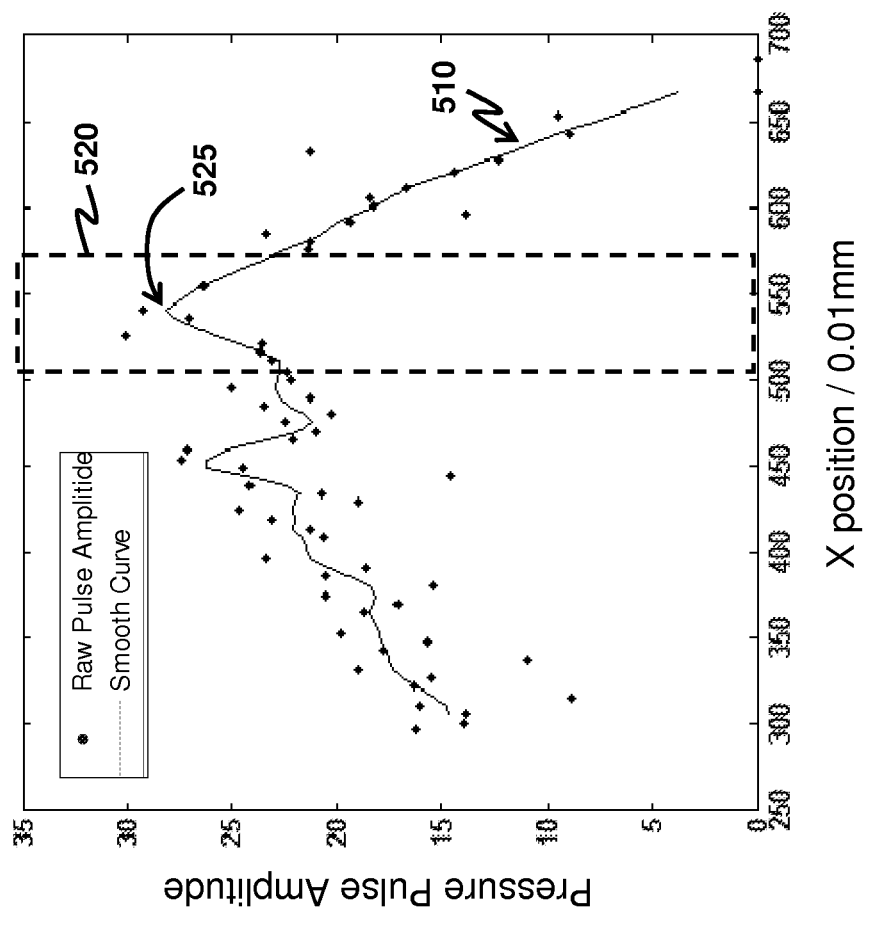
FIG. 5 is an example of determining the artery location from raw data obtained in a contact pressure search.

In one approach shown in FIG. 5, raw data of measured amplitudes are processed by a curve fitting method to from a smooth line 510, from which a maximum point 525 is identified. Since the pressure sensor 240 may not be able to be positioned exactly on the X-position of the maximum point 525 due to implementation constraints, the artery location 236 may be a location selected from a window 520 of ~0.5 mm (the effective measurement range mentioned above) enclosing the maximum point 525.

Figure 6:
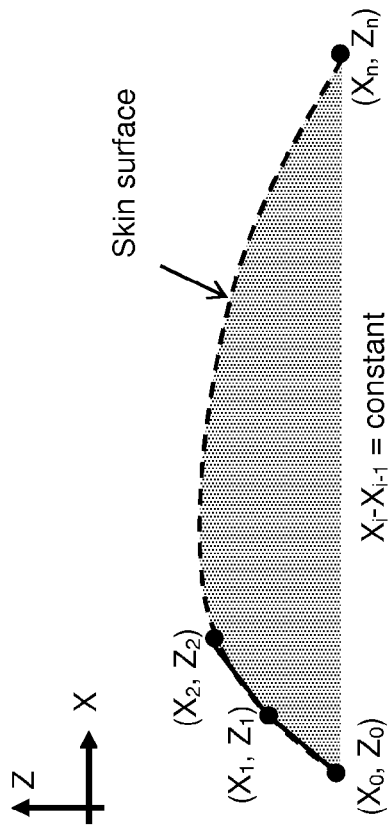
FIG. 6 provides a first flowchart as one example for illustrating how the artery location is determined by the contact pressure search.
Figure 6:
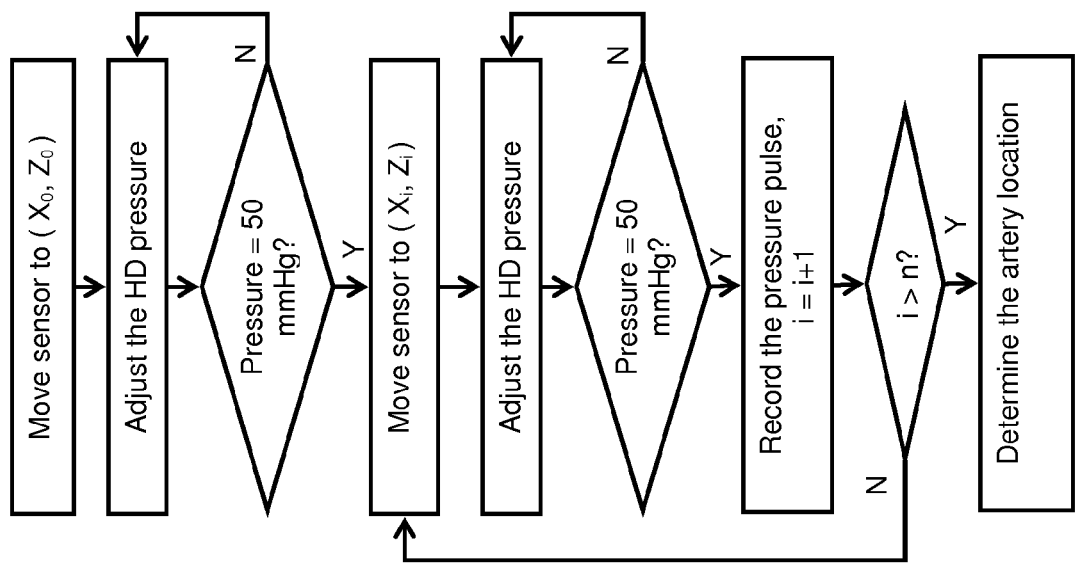

FIG. 6 is an example illustrating how the artery location 236 is determined by the contact-based process 120. During the sweeping of the pressure sensor 240 along the search region 235, the pressure sensor 240's position is finely adjusted in the Z-direction 204 to maintain the hold-down pressure to be within the pre-determined pressure range when the pressure sensor 240 reaches any of the second initial coordinates, such as $(X_1, Z_1)$, $(X_2, Z_2)$ and $(X_n, X_n)$ in FIG. 6.

Figure 7:
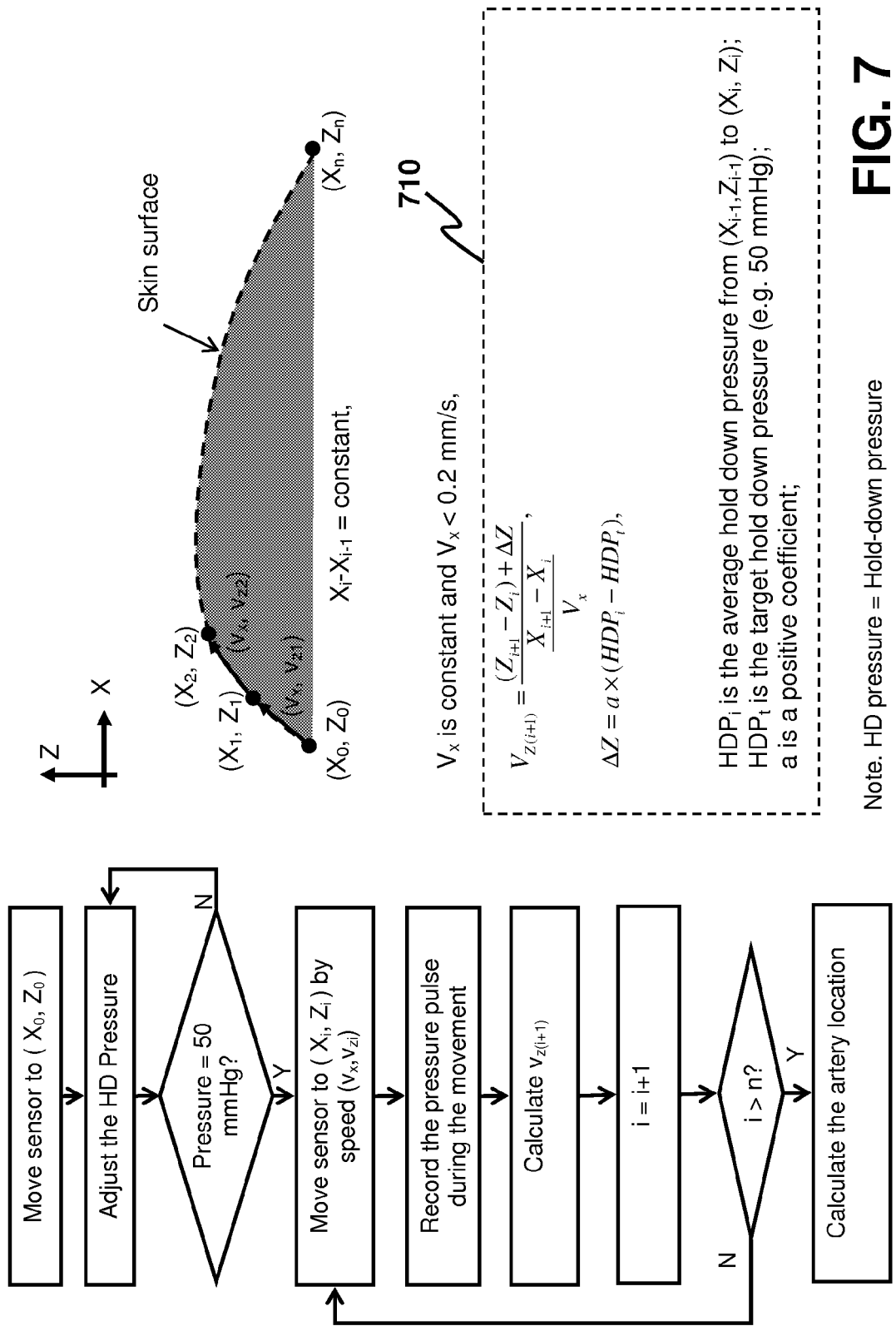
FIG. 7 provides a second flowchart as another example of the artery-location determination in the contact pressure search.

FIG. 7 gives another example of the contact-based process 120. Different from the one shown in FIG. 6, the hold-down pressure is not checked upon moving to any of the second initial coordinates. An algorithm 710, mentioned herein as an example, is employed to adjust the values of measured amplitudes for compensation of a variation in the hold-down pressure.

Figure 8:
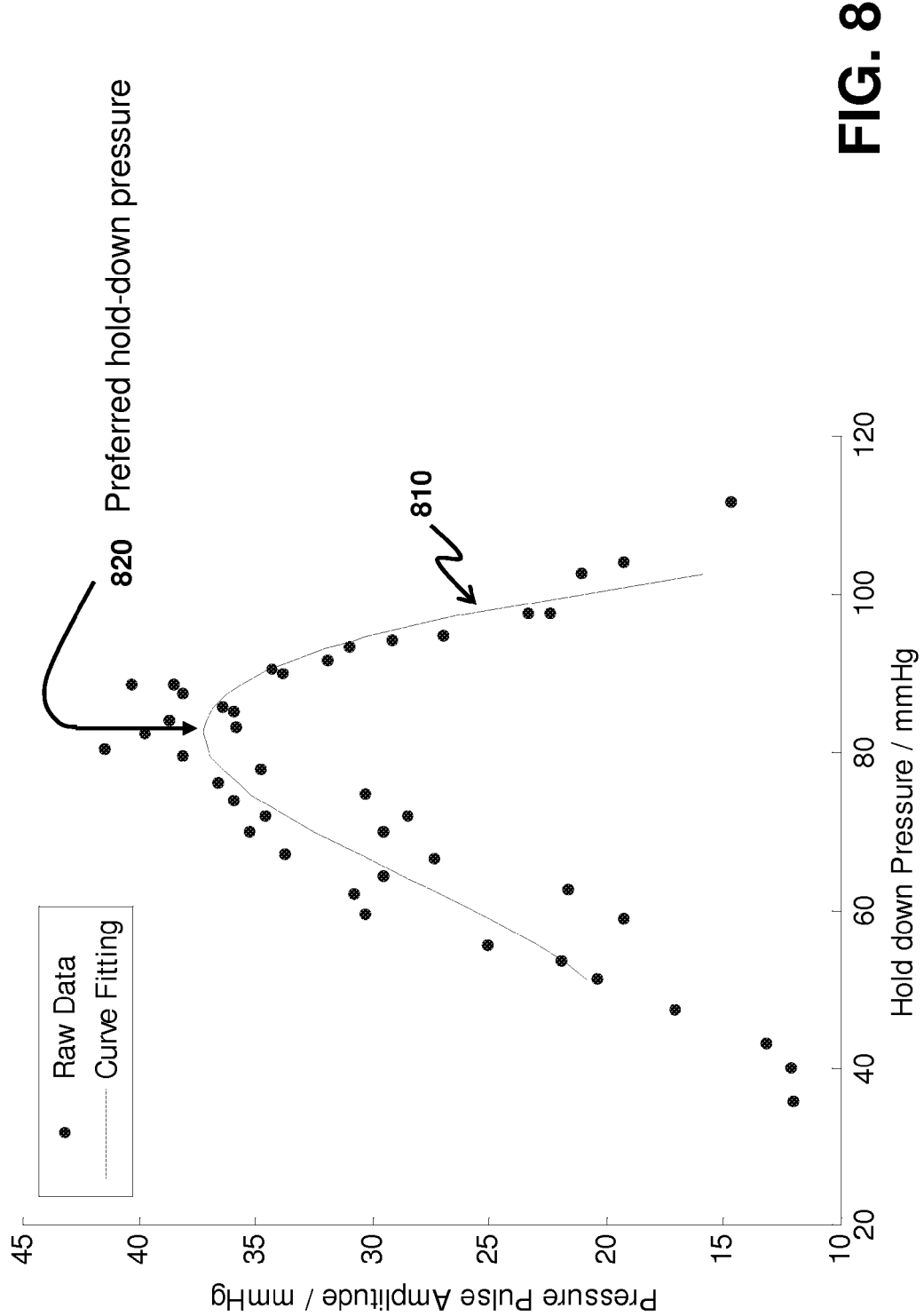
FIG. 8 is an example indicating how a preferred value of hold-down pressure is determined after the artery location is identified.

After the artery location 236 is determined and the pressure sensor 240 is positioned thereon, an optimization step, which is the optional step 140 mentioned above, can be performed by determining a preferred value of the hold-down pressure and exerting this preferred pressure value on the artery location 236. This optimization step is made by progressively increasing or decreasing the hold-down pressure while the pressure sensor 240 measures pressure pulse amplitudes at plural time instants. One approach for computing the preferred pressure value is illustrated with an aid of FIG. 8. In FIG. 8, raw data of the pressure pulse amplitudes give a smooth curve 810 by a curve-fitting technique. A maximum point 820 identified in the curve 810 is the preferred pressure value. After the preferred value is obtained, the pressure sensor 240 is fine-positioned in the Z-direction 204 so as to exert this preferred value on the artery location 236.

As shown in FIG. 2, the pressure sensor 240 and the optical-sensing unit 221 may be arranged to from one single integrated unit such that one actuator 260 is usable to move the single integrated unit in both the reference horizontal direction (the X-direction 203) and the reference vertical direction (the Z-direction 204). Alternatively, the pressure sensor 240 and the optical-sensing unit 221 may be implemented as separate units so that an actuating arrangement comprising plural actuators is used. Alternatively, the pressure sensor 240, the optical-sensing unit 221 and the actuator 260 may be integrated as one single unit and be able to move in both the reference horizontal direction (the X-direction 203) and the reference vertical direction (the Z-direction 204).

It is apparent that a tonometric BP monitoring device for measuring BP of a living subject is realizable by including a pressure sensor, a light source and an optical detector, and by configuring the device to determine an artery location on the living subject's skin and position the pressure sensor on the artery location according to the method disclosed herein.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A method for determining an artery location on a living subject's skin and positioning a tonometry pressure sensor on the artery location for measuring blood pressure of the living subject, the method comprising:

determining, by a non-contact process of using an optical-sensing unit having a light source and an optical detector to scan the skin along a scan path thereon, a search region within the scan path such that an artery is predicted to lie under the search region;

further determining a height profile characterizing the scan path's curvature by the non-contact process; and searching for the artery location within the search region by a contact-based process of sweeping the pressure sensor along the search region, wherein the sweeping of the pressure sensor along the search region is guided by curvature information provided by the height profile.

2. The method of claim 1, wherein the non-contact process comprises:

progressively scanning, by the optical-sensing unit, the skin along the scan path with a light beam generated by the light source and configured for blood sensing while the optical detector measures an instantaneous power level of the light beam reflected from the skin and a body section thereunder so that a time sequence of the measured power levels is obtained after the scanning is done;

during the scanning of the skin, controlling the optical-sensing unit's position to maintain a pre-determined distance between the unit and the scan path for eliminating a nuisance factor in obtaining the time sequence of the measured power levels, whereby after the scanning is done, a time history of the unit's coordinates is obtained and the height profile is derived therefrom; and identifying the search region within the scan path according to the time sequence of the measured power levels.

3. The method of claim 2, wherein the non-contact process further comprises:

during the scanning of the skin, estimating an instantaneous distance of the light source from the scan path by one or more selected instantaneous power levels that have been measured so as to feedback-control the unit's position to maintain the pre-determined distance between the unit and the scan path.

4. The method of claim 3, wherein the instantaneous distance is estimated according to a DC component computed from the one or more selected instantaneous power levels.

5. The method of claim 2, wherein the search region is identified according to an AC component computed from the time sequence of the measured power levels.

6. The method of claim 2, wherein the pre-determined distance is between 1 mm to 2 mm.

7. The method of claim 1, wherein the contact-based process comprises:

positioning the pressure sensor onto the search region with a hold-down pressure to be within a pre-determined pressure range, wherein a first initial coordinate of the search region for the pressure sensor to directly move to is determined according to the height profile, thereby allowing the hold-down pressure to be attained by fine-positioning the pressure sensor around the first initial coordinate;

progressively sweeping the pressure sensor along the search region to measure a pressure pulse amplitude generated by the artery so that a sequence of measured amplitudes is obtained after the sweeping is done, wherein during the sweeping, plural second initial coordinates of the search region for the pressure sensor to move to are determined according to the height profile; and within the search region, determining the artery location from the obtained sequence of measured amplitudes to thereby allow the pressure sensor to be positioned on the artery location for blood pressure measurement.

8. The method of claim 7, wherein the contact-based process further comprises:

during the sweeping of the pressure sensor along the search region, fine-positioning the pressure sensor to maintain the hold-down pressure to be within the pre-determined pressure range when the pressure sensor reaches any of the second initial coordinates.

9. The method of claim 7, wherein the pre-determined pressure range includes a nominal value selected from 30 mmHg to 100 mmHg.

10. The method of claim 1, wherein a straight-line distance over which the scan path is scanned has a length of 15 mm to 20 mm and wherein the search region has a length of 3 mm to 4 mm.

11. The method of claim 1, further comprising:

after the artery location is determined and the pressure sensor is positioned on the artery location, progressively increasing or decreasing the hold-down pressure while the pressure sensor measures pressure pulse amplitudes at plural time instants so as to compute a preferred value of the hold-down pressure from the pressure pulse amplitudes measured at said time instants; and fine-positioning the pressure sensor such that the hold-down pressure having the preferred value for blood pressure measurement is exerted on the artery location.

12. The method of claim 2, wherein the light beam comprises an infrared light component.

13. The method of claim 2, wherein the light beam is a collimated one with a beam size not greater than 2 mm.

14. A tonometric blood-pressure monitoring device for measuring blood pressure of a living subject, comprising:

an optical-sensing unit including a light source and an optical detector, the optical-sensing unit being arranged to perform a non-contact process of scanning the living subject's skin along a scan path thereon to determine:

(a) a search region within the scan path such that an artery is predicted to lie under the search region; and (b) a height profile characterizing the scan path's curvature; and a tonometry pressure sensor arranged to perform a contact-based process of sweeping the pressure sensor along the search region to search for an artery location within the search region to thereby allow the pressure sensor to be positioned on the artery location for blood pressure measurement, wherein the sweeping of the pressure sensor along the search region is guided by curvature information provided by the height profile.

15. The device of claim 14, wherein the pressure sensor and the optical-sensing unit are arranged to form one single integrated unit.

16. The device of claim 14, further comprising an actuating arrangement comprising one or more actuators for positioning the optical-sensing unit and the pressure sensor.

17. The device of claim 14, wherein the living subject is a person and the artery location is confined to an area of the skin on the person's hand or the person's wrist.

18. The device of claim 14, wherein the non-contact process comprises:

progressively scanning, by the optical-sensing unit, the skin along the scan path with a light beam generated by the light source and configured for blood sensing while the optical detector measures an instantaneous power level of the light beam reflected from the skin and a body section thereunder so that a time sequence of the measured power levels is obtained after the scanning is done;

during the scanning of the skin, controlling the optical-sensing unit's position to maintain a pre-determined distance between the unit and the scan path for eliminating a nuisance factor in obtaining the time sequence of the measured power levels, whereby after the scanning is done, a time history of the unit's coordinates is obtained and the height profile is derived therefrom;

during the scanning of the skin, estimating an instantaneous distance of the light source from the scan path by one or more selected instantaneous power levels that have been measured so as to feedback-control the unit's position to maintain the pre-determined distance between the unit and the scan path; and identifying the search region within the scan path according to the time sequence of the measured power levels.

19. The device of claim 14, wherein the contact-based process comprises:

positioning the pressure sensor onto the search region with a hold-down pressure to be within a pre-determined pressure range, wherein a first initial coordinate of the search region for the pressure sensor to directly move to is determined according to the height profile, thereby allowing the hold-down pressure to be attained by fine-positioning the pressure sensor around the first initial coordinate;

progressively sweeping the pressure sensor along the search region to measure a pressure pulse amplitude generated by the artery so that a sequence of measured amplitudes is obtained after the sweeping is done, wherein during the sweeping, plural second initial coordinates of the search region for the pressure sensor to move to are determined according to the height profile; and within the search region, determining the artery location from the obtained sequence of measured amplitudes to thereby allow the pressure sensor to be positioned on the artery location for blood pressure measurement.

20. The device of claim 19, wherein the contact-based process further comprises:

during the sweeping of the pressure sensor along the search region, fine-positioning the pressure sensor to maintain the hold-down pressure to be within the pre-determined pressure range when the pressure sensor reaches any of the second initial coordinates.

* * * * *